(12) United States Patent
Despres, III et al.

(10) Patent No.: US 8,167,954 B2
(45) Date of Patent: *May 1, 2012

(54) IMPLANT WITH COMPOSITE COATING

(75) Inventors: Alfred S. Despres, III, Davis, CA (US);
Eugene J. Elwood, Cedar Knolls, NJ (US); Robert R. Aharonov, Rockaway, NJ (US); Peter Ehlers, Allensbach (DE); Knut Andersen, Allensbach-Hegne (DE)

(73) Assignee: Consensus Orthopedics, Inc., El Dorado Hills, CA (US)

( * ) Notice: Subject to any disclaimer, the term of this patent is extended or adjusted under 35 U.S.C. 154(b) by 25 days.

This patent is subject to a terminal disclaimer.

(21) Appl. No.: 12/290,876

(22) Filed: Nov. 4, 2008

(65) Prior Publication Data
US 2009/0254191 A1    Oct. 8, 2009

Related U.S. Application Data

(63) Continuation of application No. 11/329,273, filed on Jan. 10, 2006, now Pat. No. 7,445,640, which is a continuation of application No. 09/901,310, filed on Jul. 9, 2001, now Pat. No. 7,105,030, which is a continuation of application No. 09/079,502, filed on May 14, 1998, now Pat. No. 6,261,322.

(51) Int. Cl.
*A61F 2/28* (2006.01)

(52) U.S. Cl. ................................. 623/23.53

(58) Field of Classification Search ..... 623/23.36–23.53
See application file for complete search history.

(56) References Cited

U.S. PATENT DOCUMENTS

| | | |
|---|---|---|
| 3,855,638 A | 12/1974 | Pilliar |
| 3,953,899 A | 5/1976 | Charnley |
| 4,038,703 A | 8/1977 | Bokros |
| 4,166,292 A | 9/1979 | Bokros |
| 4,216,549 A | 8/1980 | Hillberry et al. |
| 4,491,987 A | 1/1985 | Park |
| 4,718,905 A * | 1/1988 | Freeman ............ 623/6.5 |
| 4,813,959 A | 3/1989 | Cremascoli |
| 4,818,559 A | 4/1989 | Hama et al. |
| 4,978,358 A | 12/1990 | Bobyn |
| 5,074,881 A | 12/1991 | Thull et al. |
| 5,133,771 A | 7/1992 | Duncan et al. |
| 5,176,712 A | 1/1993 | Homsy |
| 5,323,954 A | 6/1994 | Shetty et al. |
| 5,368,881 A | 11/1994 | Kelman et al. |
| 5,372,130 A | 12/1994 | Stern et al. |
| 5,441,537 A | 8/1995 | Kenna |
| 5,443,523 A | 8/1995 | Mikhail |
| 5,545,227 A | 8/1996 | Davidson et al. |
| 5,549,683 A | 8/1996 | Bonutti |
| 5,569,308 A | 10/1996 | Sottosanti |

(Continued)

FOREIGN PATENT DOCUMENTS
JP    4-303443    10/1992
(Continued)

*Primary Examiner* — Suzette J Gherbi
(74) *Attorney, Agent, or Firm* — Pandiscio & Pandiscio

(57) ABSTRACT

Systems and methods are described for implants with composite coatings to promote tissue in-growth and/or on-growth. An implant includes: a substrate; a structured surface formed on at least a portion of the substrate; and a biocompatible coating deposited on at least a fraction of the structured surface. The systems and methods provide advantages in that the implant has good biocompatibility while the biocompatible coating has good strength.

2 Claims, 9 Drawing Sheets

U.S. PATENT DOCUMENTS

| | | |
|---|---|---|
| 5,603,338 A | 2/1997 | Beaty |
| 5,650,108 A | 7/1997 | Nies et al. |
| 5,658,338 A | 8/1997 | Tullos et al. |
| 5,665,118 A | 9/1997 | LaSalle et al. |
| 5,665,121 A | 9/1997 | Gie et al. |
| 5,702,448 A | 12/1997 | Buechel et al. |
| 5,711,763 A | 1/1998 | Nonami et al. |
| 5,723,011 A | 3/1998 | Devanathan et al. |
| 5,725,597 A | 3/1998 | Hwang |
| 5,746,272 A | 5/1998 | Mastrorio et al. |
| 5,770,225 A | 6/1998 | Parekh et al. |
| 5,820,707 A | 10/1998 | Amick et al. |
| 5,824,104 A | 10/1998 | Tuke |
| 5,868,796 A | 2/1999 | Buechel et al. |
| 5,876,453 A | 3/1999 | Beaty |
| 5,876,454 A | 3/1999 | Nanci et al. |
| 5,879,404 A | 3/1999 | Bateman et al. |
| 5,938,702 A | 8/1999 | Lopez et al. |
| 5,981,827 A | 11/1999 | Devlin et al. |
| 5,998,024 A | 12/1999 | Frey et al. |
| 6,008,432 A | 12/1999 | Taylor |
| 6,010,533 A | 1/2000 | Pope et al. |
| 6,045,581 A | 4/2000 | Burkinshaw |
| 6,083,570 A | 7/2000 | Lemelson et al. |
| 6,087,553 A | 7/2000 | Cohen et al. |
| 6,096,175 A | 8/2000 | Roth |
| 6,120,545 A | 9/2000 | Hamelijnck et al. |
| 6,139,585 A | 10/2000 | Li |
| 6,165,616 A | 12/2000 | Lemelson et al. |
| 6,171,343 B1 | 1/2001 | Dearnaley et al. |
| 6,228,471 B1 | 5/2001 | Neerinck et al. |
| 6,248,811 B1 | 6/2001 | Ottersbach et al. |
| 6,261,322 B1 * | 7/2001 | Despres et al. ............ 623/23.53 |
| 6,280,476 B1 | 8/2001 | Metzger et al. |
| 6,291,070 B1 | 9/2001 | Arpac et al. |
| 6,352,560 B1 | 3/2002 | Poeschmann et al. |
| 6,368,354 B2 | 4/2002 | Burstein et al. |
| 6,419,707 B1 | 7/2002 | Leclercq |
| 6,447,550 B1 | 9/2002 | Hunter et al. |
| 6,475,243 B1 | 11/2002 | Sheldon et al. |
| 6,527,919 B1 | 3/2003 | Roth |
| 6,827,742 B2 | 12/2004 | Hayes, Jr. et al. |
| 7,105,030 B2 * | 9/2006 | Despres et al. ............ 623/23.36 |
| 7,445,640 B2 * | 11/2008 | Despres et al. ............ 623/23.53 |

FOREIGN PATENT DOCUMENTS

| | | |
|---|---|---|
| WO | WO 97/16137 | 5/1997 |
| WO | WO 98/22049 | 5/1998 |

* cited by examiner

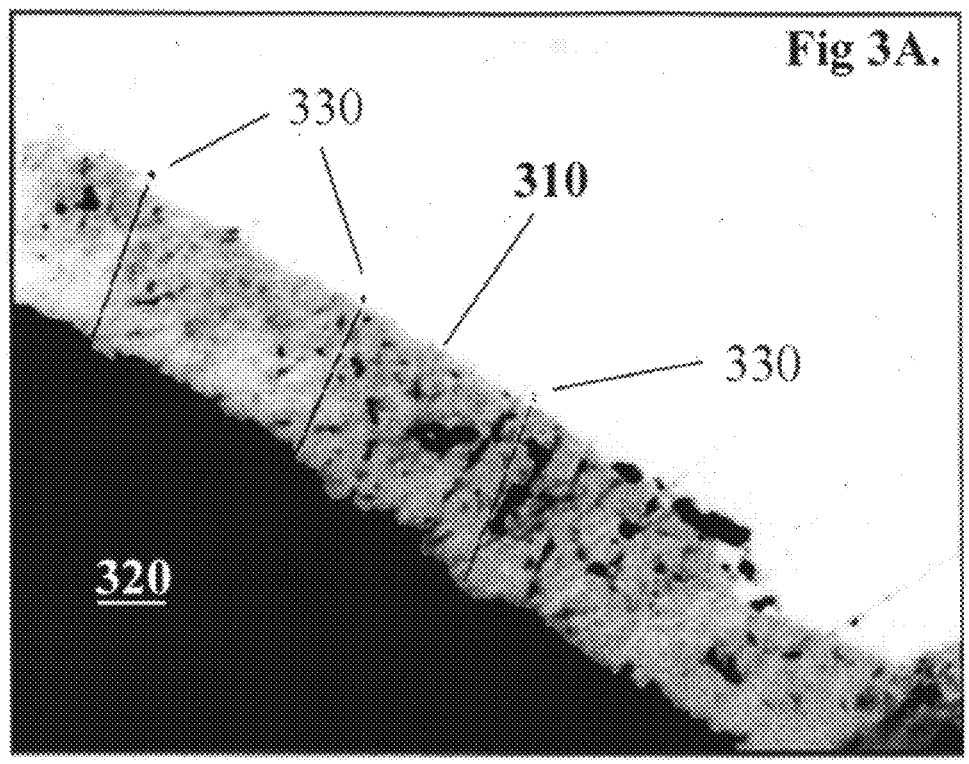
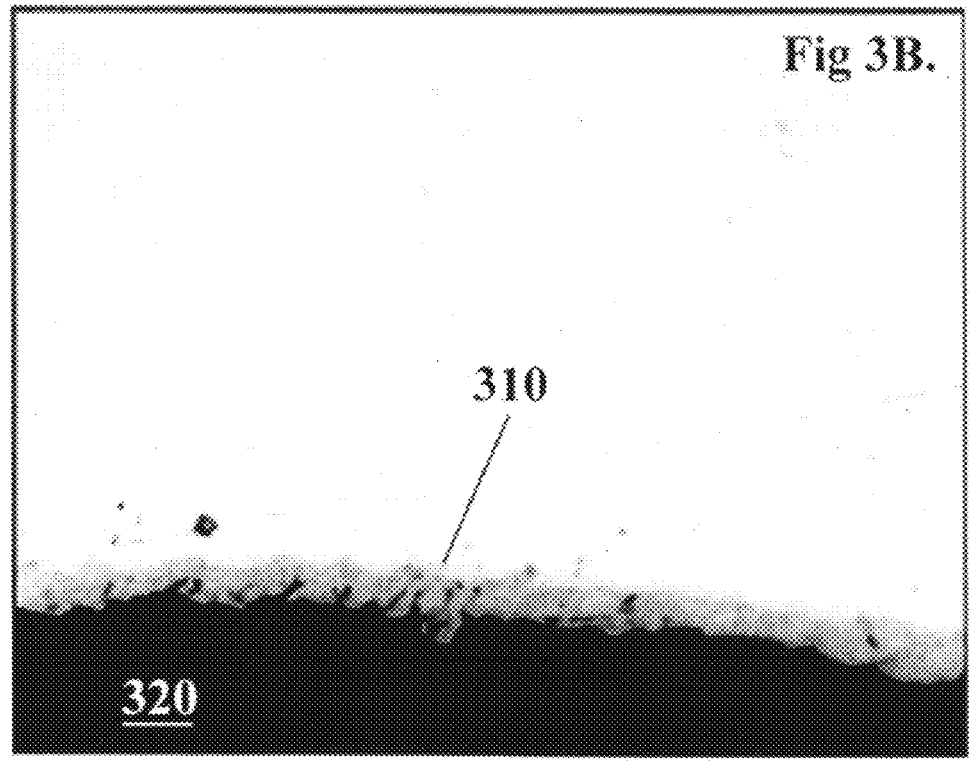

SEM Micrograph of Group B at 300x after Electrochemical Test.

SEM Micrograph of Group B at 700x after electrochemical test.

SEM micrographs of the Hayes CrCoMo sample after ASTM F746 corrosion test indicates intergranular corrosion attacks.

SEM micrographs of the Hayes CrCoMo sample after ASTM F746 corrosion test exhibiting corrosion attacks SEM micrographs of the Hayes CrCo sample prior to any corrosion test.

IMPLANT WITH COMPOSITE COATING

REFERENCE TO PENDING PRIOR PATENT APPLICATIONS

This patent application is a continuation of prior U.S. patent application Ser. No. 11/329,273, filed Jan. 10, 2006 now U.S. Pat. No. 7,445,640 by Alfred S. Despres III et al. for IMPLANT WITH COMPOSITE COATING, which patent application is in turn a continuation of prior U.S. patent application Ser. No. 09/901,310, filed Jul. 9, 2001 now U.S. Pat. No. 7,105,030 by Alfred S. Despres III et al. for IMPLANT WITH COMPOSITE COATING, which patent application is in turn a continuation of prior U.S. patent application Ser. No. 09/079,502, filed May 14, 1998 now U.S. Pat. No. 6,261,322 by Alfred S. Despres III et al. for IMPLANT WITH COMPOSITE COATING.

BACKGROUND OF THE INVENTION

1. Field of the Invention

The invention relates generally to the field of in vivo implants. More particularly, preferred embodiments of the invention are directed to an orthopedic prosthesis having a composite coating to promote tissue in-growth and/or tissue on-growth.

2. Discussion of the Related Art

Prior art implants are known to those skilled in the art. For example, conventional implants are typically composed of stainless steel, cobalt-chrome, or titanium alloy.

A problem with this technology has been that the best substrate materials are not the best materials to be in contact with living tissue. Therefore, what is required is a solution that can provide a biocompatible coating on a substrate.

One approach in an attempt to solve the above-discussed problems involves simply coating an implant substrate with a biocompatible material. However, a disadvantage of this approach is that biocompatible materials are often soft or brittle.

Another disadvantage of this approach has been relatively high cost and/or technical complexity. Therefore, what is also needed is a solution that meets the above-discussed requirements in a more simple and cost effective manner.

Heretofore, the requirements of good substrate properties, and good coating properties referred to above have not been fully met in combination. What is needed is a solution that simultaneously addresses both of these requirements.

SUMMARY OF THE INVENTION

A primary object of the invention is to provide implants with a composite coating to promote tissue in-growth and/or tissue on-growth. Another primary object of the invention is to provide a composition that can used as the composite coating. Another primary object of the invention is to provide implants having a composite coating that is located only on surface areas of the implant that are to be fixed with tissue in-growth and/or on-growth for stability. Another primary object of the invention is to provide methods of making the orthopedic implant.

In accordance with these objects, there is a particular need for an implant with a composite coating. Thus, it is rendered possible to simultaneously satisfy the above-discussed requirements of good substrate properties and good biocompatible coating properties, which, in the case of the prior art, are mutually contradicting and cannot be easily satisfied.

A first aspect of the invention is implemented in an embodiment that is based on an implant, comprising: a substrate; a structured surface defined by at least a portion of said substrate; and a biocompatible coating deposited on at least a fraction of said structured surface. A second aspect of the invention is implemented in an embodiment that is based on a composition for an implant, comprising: a biocompatible material coated on a structured surface defined by a substrate. A third aspect of the invention is implemented in an embodiment that is based on an implant, comprising: a substrate; a structured surface defined by a portion of said substrate; and a biocompatible coating deposited on at least a fraction of said structured surface, wherein said portion of said substrate is to be fixed with tissue in-growth and/or on-growth for stability. A fourth aspect of the invention is implemented in an embodiment that is based on a method of forming a composite coating, comprising: depositing a biocompatible coating on a structured surface defined by at least a portion of a surface area of a substrate.

These, and other, objects and aspects of the invention will be better appreciated and understood when considered in conjunction with the following description and the accompanying drawings. It should be understood, however, that the following description, while indicating preferred embodiments of the invention and numerous specific details thereof, is given by way of illustration and not of limitation. Many changes and modifications may be made within the scope of the invention without departing from the spirit thereof, and the invention includes all such modifications.

BRIEF DESCRIPTION OF THE DRAWINGS

A clear conception of the advantages and features constituting the invention, and of the components and operation of model systems provided with the invention, will become more readily apparent by referring to the exemplary, and therefore nonlimiting, embodiments illustrated in the drawings accompanying and forming a part of this specification, wherein like reference characters (if they occur in more than one view) designate the same parts. It should be noted that the features illustrated in the drawings are not necessarily drawn to scale.

FIGS. 3a-3b illustrate micrograph views of a physical vapor deposited coating of titanium on a structured surface of cobalt-chrome alloy, representing an embodiment of the invention.

DESCRIPTION OF PREFERRED EMBODIMENTS

Figure 1:
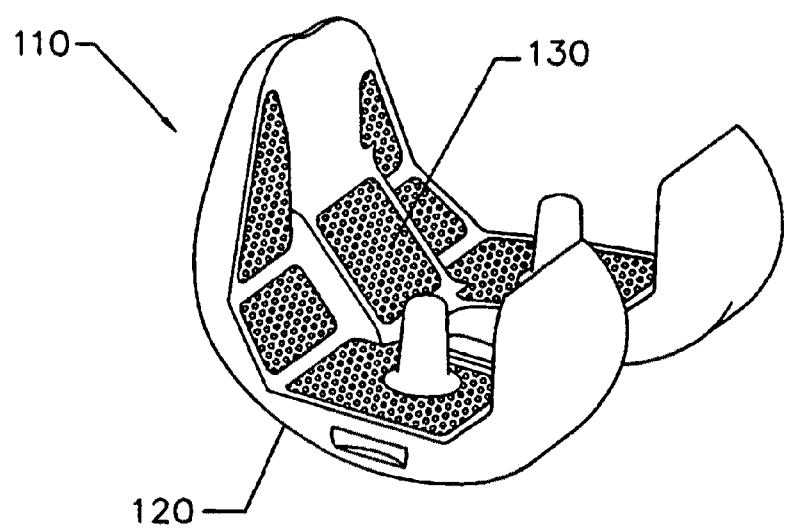
FIG. 1 illustrates a schematic perspective view of an orthopedic implant, representing an embodiment of the invention.

The invention and the various features and advantageous details thereof are explained more fully with reference to the nonlimiting embodiments that are illustrated in the accompanying drawings and detailed in the following description. Descriptions of well known components and processing techniques are omitted so as not to unnecessarily obscure the invention in detail.

The context of the invention is providing an implant to be positioned in vivo during surgery, especially orthopedic surgery to replace a joint, such as, for example, a knee joint or a hip joint. Thus, the implant can be used in a method for orthopedic surgery that includes surgically positioning the implant within a vertebrate in need thereof. If bone growth is facilitated, the implant can be termed part of an osteoconductive process that includes contacting a bone under in vivo conditions with the implant.

Referring to the drawings, a detailed description of preferred embodiments of the invention is provided with respect to FIGS. 1 through 5. The invention is not limited to the specific embodiments illustrated in FIGS. 1-5.

Referring now to FIG. 1, a component 110 of an artificial knee joint is depicted. The component 110 includes a bearing surface 120 and a tissue fixation surface 130. The bearing surface 120 is for sliding. The tissue fixation surface 130 is for tissue in-growth and/or tissue on-growth. The tissue fixation surface 130 can be a coating that is deposited on at least a fraction of a structured surface that is defined by, or formed on, or composed by at least a portion of a substrate.

The substrate can be composed, or formed, of, for example, carbon-composite, stainless steel, cobalt-chromium, titanium alloy, tantalum, and/or ceramic, and combinations thereof. The structured surface can be defined by, or composed of, or formed of a material that includes a plurality of particles that are sintered together to form a continuous porous phase. Alternatively, the structured surface can be prepared by at least one method selected from the group consisting of flame spraying, acid etching, grit blasting, casting-in, forging-in, laser texturing, and micromachining.

The coating should be a biocompatible coating. The biocompatible coating can include one, or more, of titanium, tantalum, carbon, calcium phosphate, zirconium, niobium, hafnium, hydroxyapatite, tissue in-growth and/or on-growth facilitating proteins, and combinations thereof. If carbon is used, it can optionally be diamond-like carbon, pyrolytic carbon, amorphous diamond-like carbon, and combinations thereof.

It can be advantageous that the coating be more biocompatible than the structured surface. Similarly, it can be advantageous that the coating be more biocompatible than the substrate. One aspect, albeit optional, of biocompatibility is softness. It can be advantageous that the coating be softer than the structured surface. Similarly, it can be advantageous that the coating be softer than the substrate. Although the preferred embodiment shown in FIG. 1 includes a coating located on specific portions of the substrate, it is within the level of ordinary skill in the art after having knowledge of the invention disclosed herein to coat any surface(s) of the substrate.

Figure 2:
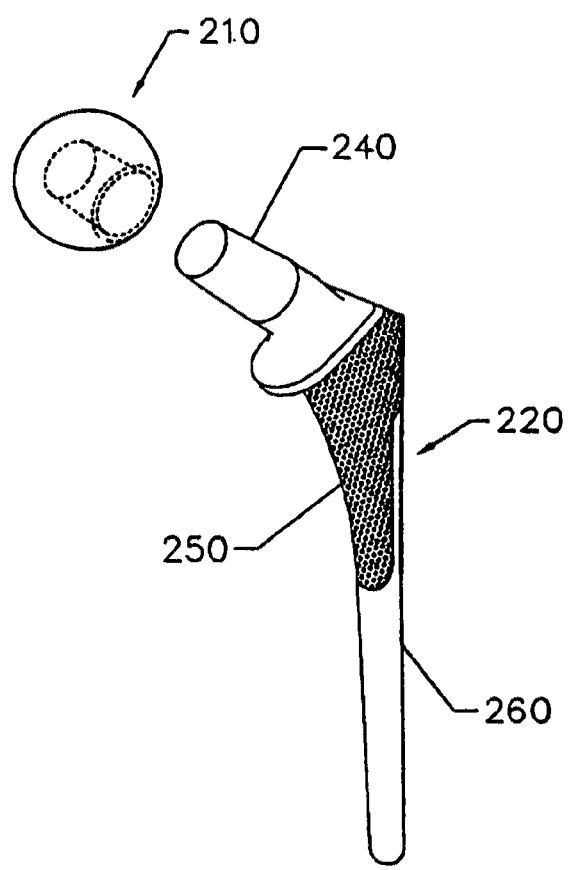
FIG. 2 illustrates a schematic perspective view of an orthopedic implant, representing an embodiment of the invention.

Referring now to FIG. 2, an artificial hip joint is depicted. The hip joint includes a femoral head 210 and distal portion 220. The femoral head 210 includes a joint motion surface 230 for bearing and sliding. The distal portion 220 includes a taper connection 240, a tissue fixation surface 250, and a distal stem 260. The tissue fixation surface 250 can be a coating that is deposited on at least a fraction of a structured surface that is defined by, or formed on, or composed by at least a portion of a substrate. As noted above, the coating should be a biocompatible coating. The biocompatible coating can include multi-layers. These multi-layers can be nano-layers. Although the preferred embodiment shown in FIG. 2 includes the coating located on a specific portion of the substrate, it is within the level of ordinary skill in the art after having knowledge of the invention disclosed herein to coat any surface(s) of the substrate.

Referring now to FIGS. 3a-3b, two images of a structured surface coated according to the invention are depicted. FIGS. 3a-3b are two images of the same sample acquired at different locations. FIG. 3a illustrates a coating 310 on a structured surface 320 at an outermost location. The structure surface 320 is defined by a sintered layer having interconnected porosity. The thickness of the coating 310 is approximately 10.78 microns at this outermost location of the structured surface 320. FIG. 3b illustrates the coating 310 on the structured surface 320 at an innermost location. The thickness of the coating is approximately 2.0 microns at this innermost location of the structured surface 320.

Still referring to FIGS. 3a-3b, a coating 310 is adhered to a structured surface 320. In this particular embodiment, the coating 310 is composed of a first material that includes titanium. The coating is preferably a biocompatible coating. In this particular embodiment, the structured surface 320 is defined by a second material that includes cobalt and chrome. In this particular embodiment, the structured surface was conditioned by cathodic arc ion plating of titanium before the coating 310 was deposited using the same apparatus used to effect the ion plating. In this particular embodiment, the average thickness of the coating 310 is approximately 10.78 microns. If the structured surface 320 includes crevices and/or undercuts 330, the biocompatible material that composes the coating 310 can coat the crevices and/or undercuts 330 in the structured surface.

It can be advantageous if the biocompatible material conforms to the crevices and/or undercuts and thereby defines a textured (e.g., rough) topology at the upper surface of the biocompatible material. This is advantageous because such a topology gives tissue a better hold via tissue in-growth and/or on-growth. Further, if there are pores in and/or beneath the structured surface the, biocompatible material can coat the pores. It can be advantageous if the biocompatible material coats interconnected pores located beneath the structured surface and thereby define voids (pores) and/or interconnected pores in which tissue in-growth and/or on-growth can occur.

The effect of cathodic arc ion plating with a high bias voltage is to cause an intermixing of titanium into the cobalt-chrome substrate due to high ion energies. It can be appreciated that there is an inter-penetration of the coating material into the structured surface material between the interface and the bulk of the material that composes the structured surface. Specifically, the amount of coating material that composes the substrate that defines the structured surface decreases as the depth from the interface increases. When the bias voltage is increased, the inter-penetration depth increases. The depth of this intermixing can range from approximately 0.5 nm to approximately 500 nm, preferably approximately 50 nm to approximately 100 nm. When the bias voltage is sufficient, substantial inter-penetration occurs. This result is advantageous because the inter-penetration improves the adhesion of the coating to the structured surface, thereby minimizing flaking, peeling, and other disruptions of the coating. This is very important for at least the following two reasons. First, the coating will be subject to tissue in-growth and/or on-growth and, therefore, can be subject to dynamic loading from adjacent tissue structures, such as, for example, bones. By improving the adhesion, the coating is better able to withstand loading. Second, the implant may be expected to remain in vivo for many years and it is highly desirable that all of the implant remain fixed in place. By improving the adhesion of the coating to the structured surface, the long term stability of the coating is enhanced.

Figure 4:
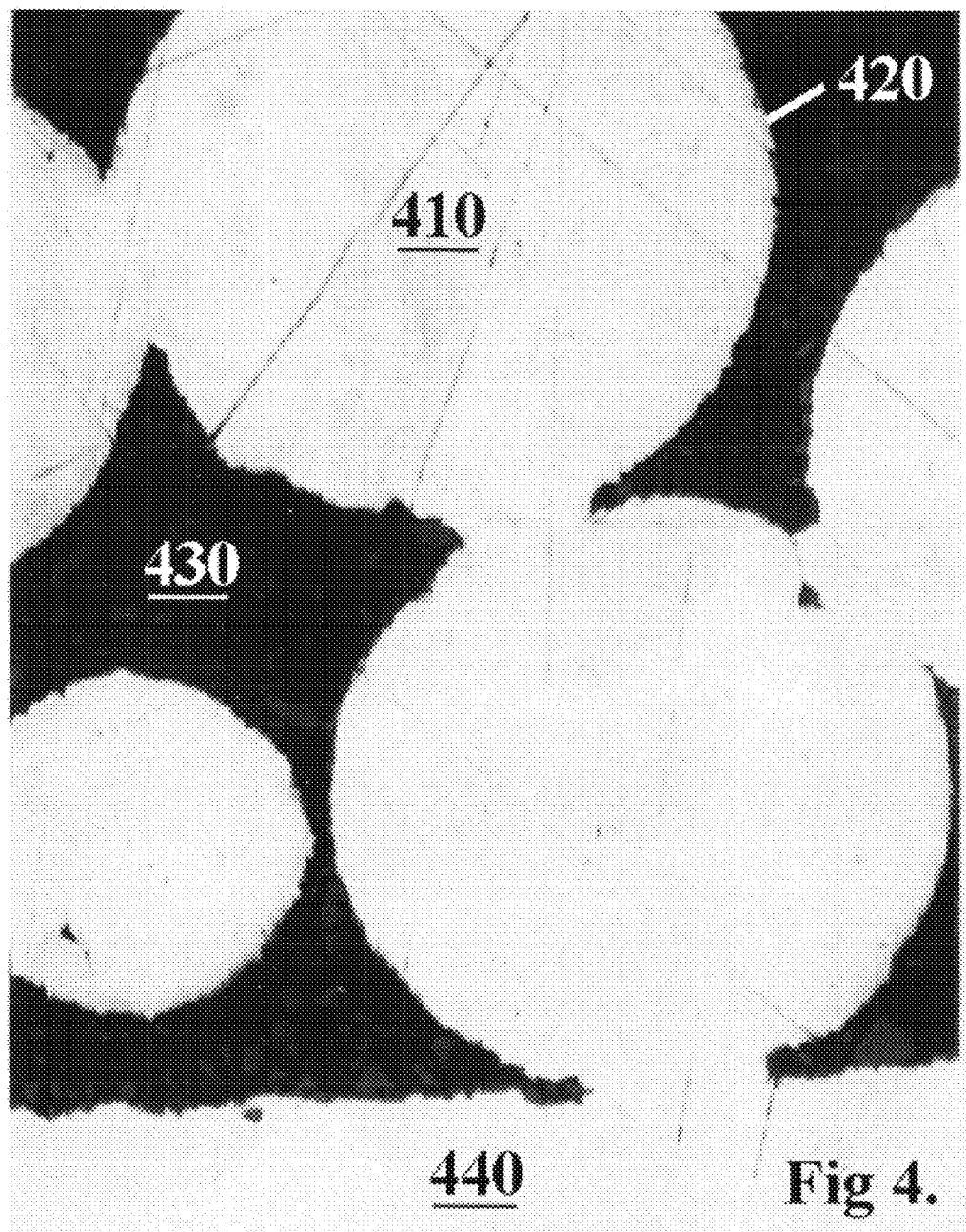
FIG. 4 illustrates a schematic view of a coating on a porous structured surface, representing an embodiment of the invention.

Referring now to FIG. 4, a porous structured surface 410 with a coating 420 is depicted. The coating 420 includes titanium and can be deposited via physical vapor deposition with a gas, preferably an inert gas, such as, for example, argon and/or helium. It can be advantageous to use argon as the gas because it is inert and has a relatively high atomic weight. Significantly, the coating 420 covers portions of a structured surface defined by an interconnected pore 430 that is hidden from line-of-sight deposition (i.e., the pore 430 cannot be seen from the point of view of the deposition source). The structured surface is also defined by a plurality of particles covering a substrate 440 (i.e., the structured surface is defined by the interface between the substrate 440 and the plurality of particles). Nevertheless, the surface defined by the interconnected pore 430 is coated and provides an area for tissue in-growth and/or on-growth because an inert gas is present in the deposition chamber while the coating 420 is being applied. Although the preferred embodiment shown in FIG. 4 includes the coating of the surface defined by the interconnected pore 430, it is within the level of ordinary skill in the art after having knowledge of the invention disclosed herein to coat any undercut, or vertical, or line-of-sight hidden surface area.

FIG. 4 demonstrates substantially improved results that are unexpected. Specifically, the coating of internal pores demonstrates the significant unexpected advantageous result that when an inert gas is present during the deposition process, the coating is deposited on line-of-sight hidden surfaces (e.g. interconnected pores). It can be appreciated that the structured surface 410 is coated because the exterior of the particles appears rough. Normally, in the case of an uncoated particle, the perimeter would be smooth and more nearly circular. The roughness is the coating. This result is advantageous because it significantly improves adhesion of the surrounding tissue to the implant. Adhesion is significantly improved because tissue on-growth and/or in-growth can take place on undercuts, crevices, cul de sacs, conduits, caves, tunnels, and interconnected pores that are hidden from line-of-sight deposition, thereby significantly improving the strength of the connection between the surrounding tissue and the implant. The strength of the connection is significantly improved because the tissue grows into the undercuts, crevices, cul de sacs, conduits, caves, tunnels, and interconnected pores creating a tissue structure that interlocks with the structured surface on a macroscopic level. It can be advantageous if the coating covers a continuous length of a void structure (e.g., undercuts, crevices, cul de sacs, conduits, caves, tunnels, interconnected pores, etc.) that is open to adjacent tissue in at least two places. For example, if the tissue grows through a tunnel, the strength of the connection will be based not only on the interface adhesion between the wall of the tunnel and the tissue, but also on the inherent mechanical strength of the loop of tissue that is routed through the tunnel.

The particular manufacturing process used for depositing the coating should be inexpensive and reproducible. Conveniently, the deposition of the coating can be carried out by using any vapor deposition method. Vapor deposition methods include chemical vapor deposition (CVD) (e.g., plasma assisted CVD) and physical vapor deposition (PVD) (e.g., arc evaporation, e-beam, molten pool, sputtering, evaporative ion plating, and cathodic arc ion plating). It is preferred that the process be a physical vapor deposition. For the manufacturing operation, it is moreover an advantage to employ an arc evaporation physical vapor deposition method.

Figure 5:
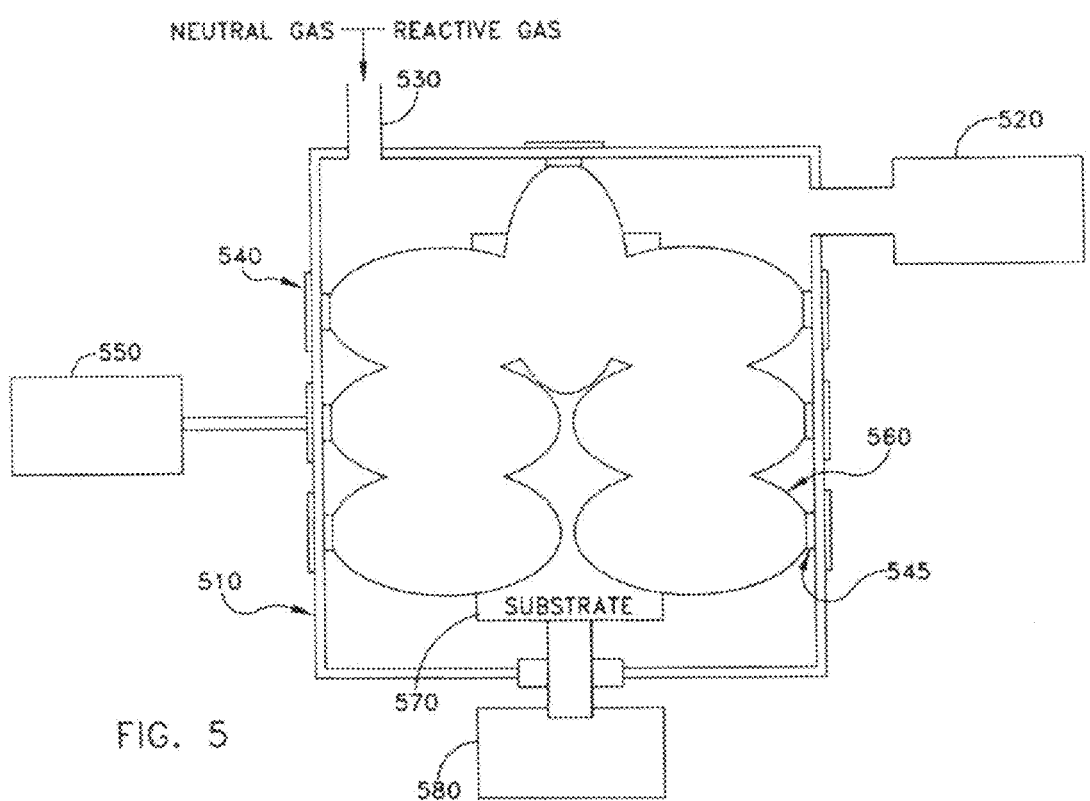
FIG. 5 illustrates a schematic view of an apparatus and process for coating a structured surface, representing an embodiment of the invention.

FIG. 5 depicts an arc evaporation physical vapor deposition apparatus and method for coating a structured surface on a substrate. A water cooled chamber 510 functions as an anode. A vacuum pump 520 and a conduit 530 for a neutral gas and a reactive gas are connected to the chamber 510. The chamber includes a plurality of evaporators 540 that function as cathodes. Each of the evaporators includes a source of a material 545 from which the coating is to be formed (e.g., titanium). An arc power supply 550 can be connected to each of the plurality of evaporators 540 (only a single connection is shown in FIG. 5). Each of the evaporators 540 can generate a plasma 560 that includes a high number of ions together with electrons and neutral vapor atoms. (It should be noted that the plasma 560 is represented schematically for clarity.) The plasma 560 impinges upon a substrate 570 that is connected to a bias (−) power supply. By increasing the bias, the ions are accelerated toward the substrate more rapidly. The apparatus can also include one, or more, structures to steer and/or filter the plasma such as, for example internal and/or external magnets.

Still referring to FIG. 5, the substrate 570 includes a structured surface (not shown) onto which the coating can be deposited. Portions of the substrate that are not to be coated can be masked with a mask material that can be removed after the deposition of the coating is finished. In general, the coating can be formed by any thin film technique. Thin film technique include physical vapor deposition and chemical vapor deposition, and combinations thereof.

Still referring to FIG. 5, the method of using the illustrated apparatus begins by loading the substrate 570 into the chamber 510. A vacuum is then created in the chamber 510 using the vacuum pump 520. A test for leaks is then conducted. A conditioning and heating subprocess can then be performed. One reason to conduct this subprocess is to heat and remove any oxides from the structured surface. This subprocess can be based on radiant heating. This subprocess can also be based on glow discharge with a high bias voltage to effect an ion bombardment by a gas, or gas mixture. This subprocess can also be based on ion bombardment with the material from which the coating is to be formed (e.g., titanium) with a high bias voltage (e.g., from approximately 1000 to approximately 1500 volts). This latter technique causes an intermixing of the coating material (e.g., titanium) into the material that defines the structured surface (e.g., CoCr). After the conclusion of the subprocess, the coating is applied. The bias voltage is lowered to deposit and build up the coating. By adding a gas, preferably an inert gas, such as, for example, argon or helium (most preferably argon), full coverage of undercuts and full coverage within pore structures can be obtained.

While not being limited to any particular theory, it is believed that the presence of the gas reduces the average velocity and increases the scattering of the coating vapor as it moves from the cathode to the structured surface, thereby allowing better migration of the coating vapor inside the undercuts, crevices, cul de sacs, conduits, caves, tunnels, interconnected pores, etc., before the vapor is deposited (i.e., fixed) on the structured surface. This relationship may be due to an increase in scattered vector components representing the speed and direction of the vapor molecules due to collisions between the vapor molecules and the gas molecules, with a corresponding decrease in the magnitude of a primary vector representing the average speed and velocity of all the vapor molecules.

Still referring to FIG. 5, the process temperature can range from approximately 500 to approximately 900 deg. F. The operating pressure during radiant heating can range from approximately 1.0 millitorr to approximately 0.01 millitorr. The operating pressure during the bombard phase (e.g., titanium without any dampening gas) can range from approximately 10.0 millitorr to approximately 0.001 millitorr. The operating pressure during the coating phase (e.g., titanium with optional dampening gas) can range from approximately less than 1 millitorr to approximately 100 millitorr. The arc voltage can range from approximately 10 to approximately 100 volts/evaporator. The bias voltage can range from approximately 1000 to approximately 1500 volts during bombardment, and from approximately 10 to approximately 500 volts during coating.

However, the particular manufacturing process used for depositing the coating is not essential to the invention as long as it provides the described biocompatible coating. Normally those who make or use the invention will select the manufacturing process based upon tooling and energy requirements, the expected application requirements of the final product, and the demands of the overall manufacturing process.

Figure 6A:
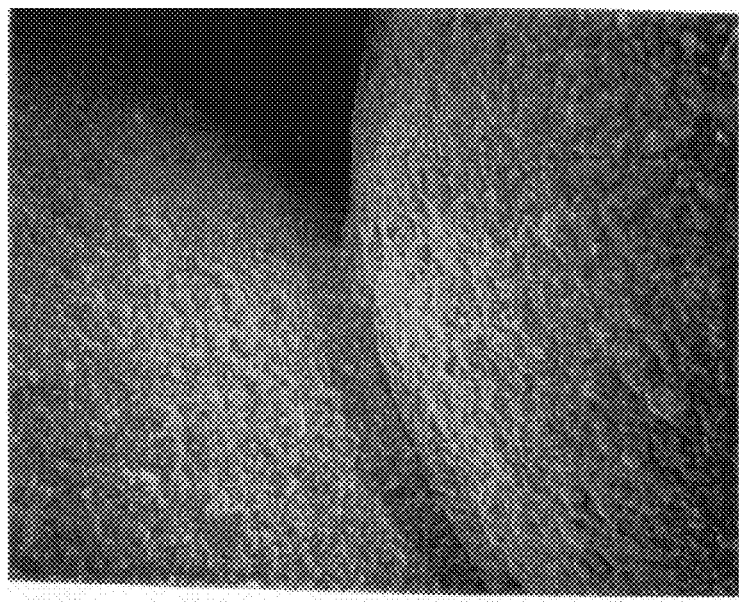
FIGS. 6a-6b illustrate scanning electron micrographs of a biocompatible coating on CoCrMo particles after an electrochemical test, representing an embodiment of the invention.
Figure 6B:
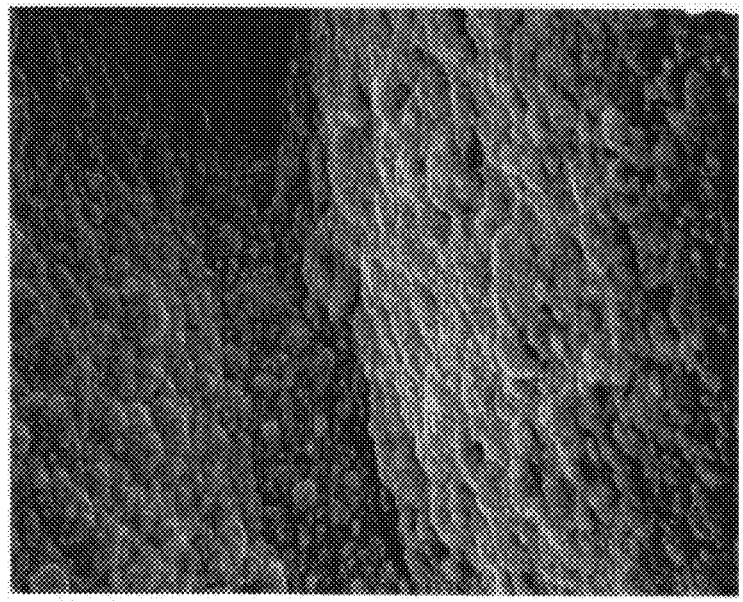

Referring now to FIGS. 6a-6b, scanning electron micrographs of a biocompatible coating including titanium on a structured surface defined by CoCrMo particles after an electrochemical test (ASTM F746) are depicted. FIG. 6a was acquired at ×300. FIG. 6b was acquired at ×700.

Figures 7A, 7B:
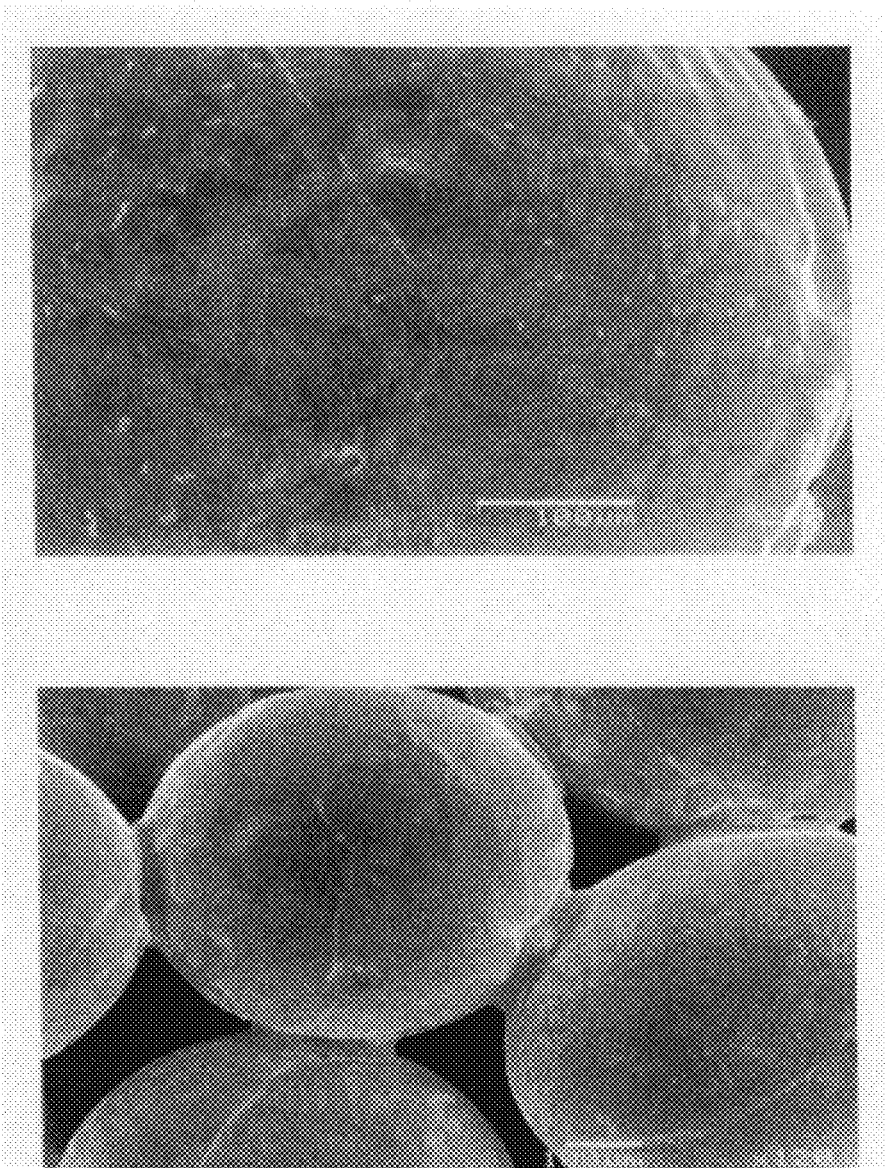
FIGS. 7a-7d illustrate scanning electron micrographs of CoCrMo particles without the biocompatible coating after the electrochemical test, representing an embodiment of the invention.
Figures 7C, 7D:
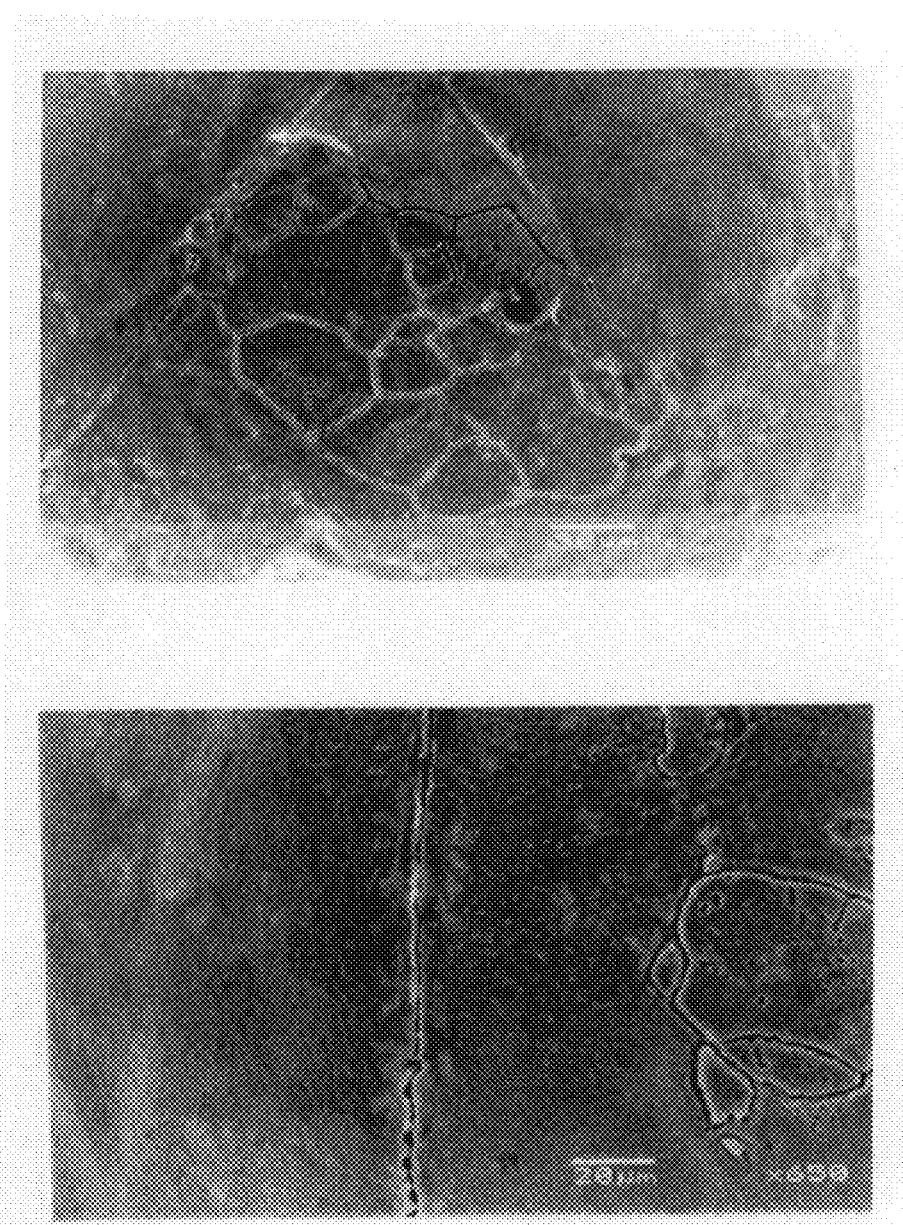

Referring now to FIGS. 7a-7d, electron micrographs of a structured surface defined by CoCrMo particles without the biocompatible coating after the electrochemical test (ASTM F746) are depicted. FIG. 7b was acquired at ×120. FIG. 7d was acquired at ×650.

By comparing the results shown in FIGS. 7a-7b with the results shown in FIGS. 6a-6b, it can be appreciated that the biocompatible coating significantly inhibits corrosion. For example, FIGS. 7a-7d show significant evidence of intergranular corrosion attacks while FIGS. 6a-6b do not show significant evidence of intergranular corrosion attacks.

Figures 8A, 8B:
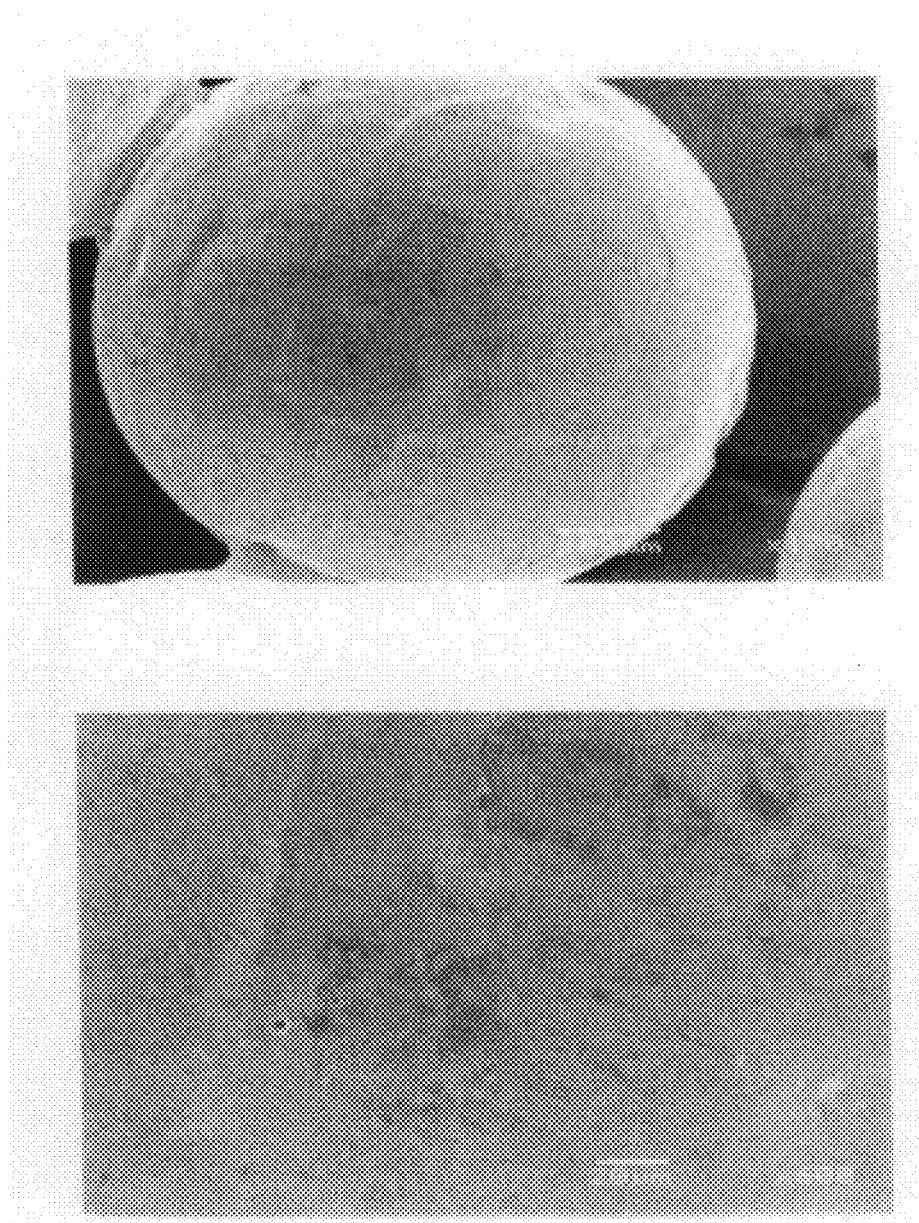
FIGS. 8a-8b illustrate SEM of CoCrMo particles without coating before test, representing an embodiment of the invention.

Referring now to FIGS. 8a-8b, electron micrographs of a structured surface defined by CoCrMo particles without the biocompatible coating before the electrochemical test (ASTM F746) (i.e., before any corrosion test) are depicted. FIG. 8a was acquired at ×120. FIG. 8b was acquired at ×600.

The particular material used for the substrate should be strong. Some examples of substrate materials include ASTM F67, F75, F90, F136, F138, F560, F562, F620, F621, F799, F961, F1058, F1295, F1341, F1472, F1537, and F1586. These are all grades of titanium, CoCr, stainless steel, tantalum, or alloy(s) thereof. It is preferred that the substrate material be a cobalt-chrome alloy. The substrate can be manufactured as a wrought, forged, or cast form.

The particular material used to define the structured surface should also be strong. It is preferred that the material used to define the structured surface be the same as the material used for the substrate (e.g., cobalt-chrome). However, the material used to define the structured surface can be different and include any one or more of, for example, titanium, CoCr, stainless steel, and tantalum, or alloy(s) thereof. The structured surface can be manufactured in various forms, including, but not limited to, sintered, flame sprayed, acid etched, grit blasted, cast-in, forged-in, laser textured, or micromachined form. For the manufacturing operation, it is an advantage to employ a partially sintered (porous) structure obtained by forming a layer of a mixture that contains a plurality of particles and a binder, and optionally a sacrificial filler.

For non-interconnecting (nonporous) structures, the surface roughness ($R_a$ or $R_z$) of the structured surface can range from approximately 100 to approximately 40,000 μ/inch, preferably from approximately 3,000 to approximately 30,000 μ/inch. When the structured surface is defined by a porous layer, the layer can have a thickness from approximately 0.010 to 0.080 inch deep, preferably from approximately 0.010 to 0.060 inch deep. In the case of porous structures, the pore sizes can be from approximately 50 to approximately 500 microns, preferably from approximately 200 to 450 microns.

The particular material used for the coating should be biocompatible and provide a suitable surface for tissue in-growth and/or on-growth. It is preferred that the coating be titanium. However, the coating can include one or more of, for example, titanium, tantalum, calcium phosphate, hydroxyapatite, and tissue in-growth and/or on-growth promoting proteins, or alloys thereof.

When the thickness of the coating is excessively thin, parts of the structured surface may not be covered. On the other hand, when the thickness of the coating is excessively high, the strength of the coating may go down due to residual, thermal induced stress. For the specific embodiment of pure titanium on a structured surface defined by a sintered plurality of particles with interconnected porosity, in the deepest region (e.g., bottom of the lowest pore), the minimum coating thickness can be approximately 1 micron. In the outermost region (e.g., top of the highest particle), the maximum coating thickness can be approximately 20 microns.

However, the particular materials selected for coating and substrate are not essential to the invention, as long as they provide the described functions. Normally, those who make or use the invention will select the best commercially available materials based upon the economics of cost and availability, the expected specific application requirements of the final product, and the demands of the overall manufacturing process.

The disclosed embodiments show a continuous coating deposited in one or more zones across at least a portion of a structured surface as the structure for performing the function of facilitating tissue in-growth and/or on-growth. However, the structure for promoting tissue in-growth and/or on-growth can be any other structure capable of performing the function of achieving tissue adhesion, including, by way of example, a pattern such as an array of dots, or lines, or any other geometric pattern.

While not being limited to any particular performance indicator or diagnostic identifier, preferred embodiments of the invention can be identified one at a time by testing for the presence of high adhesion between the coating and the structured surface. The test for the presence of high adhesion can be carried out without undue experimentation by the use of simple and conventional tribological and mechanical experiments. Among the other ways in which to seek embodiments having the attribute of high adhesion guidance toward the next preferred embodiment can be based on the presence of high coating coverage of undercut surfaces (e.g., hidden interconnected pores). The test for the presence of high coating coverage of undercut surfaces can be carried out without undue experimentation by the use of simple and conventional optical and/or electron microscope imaging techniques.

PRACTICAL APPLICATIONS OF THE INVENTION

A practical application of the invention that has value within the technological arts is the fabrication of an implant for the replacement of a knee joint or a hip joint. Further, the invention is useful in conjunction with other implants (such as pins used for the purpose of joining bones), or the like. There are virtually innumerable uses for the invention, all of which need not be detailed here.

ADVANTAGES OF THE INVENTION

An implant, representing an embodiment of the invention, can be cost effective and advantageous for at least the following reasons. The implants are simple and economical to implement. The implants have increased strength due to the structured surface being defined by a high strength material and better biocompatibility due to the use of materials for the coating that are more biocompatible than the substrate. A single implant can posses different surface areas that are individually optimized with i) some areas bearing tissue in-growth and/or on-growth composite coating, ii) some areas exhibiting the properties of the substrate material(s), and iii) some areas bearing hard surfaces formed by treatments, such as, for example, ion bombardment.

All the disclosed embodiments of the invention described herein can be realized and practiced without undue experimentation. Although the best mode of carrying out the invention contemplated by the inventors is disclosed above, practice of the invention is not limited thereto. Accordingly, it will be appreciated by those skilled in the art that the invention may be practiced otherwise than as specifically described herein.

For example, the individual components need not be formed in the disclosed shapes, or assembled in the disclosed configuration, but could be provided in virtually any shape, and assembled in virtually any configuration. Further, the individual components need not be fabricated from the disclosed materials, but could be fabricated from virtually any suitable materials. Further, although the implant described herein is a physically separate module, it will be manifest that the implant may be integrated into additional apparatus with which it is associated. Furthermore, all the disclosed elements and features of each disclosed embodiment can be combined with, or substituted for, the disclosed elements and features of every other disclosed embodiment except where such elements or features are mutually exclusive.

It will be manifest that various additions, modifications and rearrangements of the features of the invention may be made without deviating from the spirit and scope of the underlying inventive concept. It is intended that the scope of the invention as defined by the appended claims and their equivalents cover all such additions, modifications, and rearrangements. The appended claims are not to be interpreted as including means-plus-function limitations, unless such a limitation is explicitly recited in a given claim using the phrase "means-for." Expedient embodiments of the invention are differentiated by the appended subclaims.

What is claimed is:

1. An orthopedic implant for in vivo disposition adjacent a bone, the implant comprising:
   a substrate having a bearing surface adapted for sliding engagement with the bone;
   a structured surface formed on a portion of said substrate and adapted for engagement with tissue;
   a biocompatible coating disposed on said structured surface, the coating being more biocompatible than said structured surface and said substrate; and
   said coating being softer than said structural surface.

2. An orthopedic implant for disposition adjacent a bone, the implant comprising:
   a substrate having a bearing surface adapted for sliding engagement with a bone;
   a structured surface formed on a portion of said substrate and adapted for engagement with tissue;
   a biocompatible coating deposited on at least a fraction of said structured surface, the coating being more biocompatible than said structured surface and said substrate;
   wherein said portion of said biocompatible coating on said substrate is adapted to accommodate tissue in-growth and/or on-growth for stability.

* * * * *